United States Patent [19]

Wang

[11] Patent Number: 6,004,755
[45] Date of Patent: Dec. 21, 1999

[54] QUANTITATIVE MICROARRAY HYBRIDIZATON ASSAYS

[75] Inventor: Bruce Wang, Pacifica, Calif.

[73] Assignee: Incyte Pharmaceuticals, Inc., Palo Alto, Calif.

[21] Appl. No.: 09/056,338

[22] Filed: Apr. 7, 1998

[51] Int. Cl.$^6$ ........................................... C12Q 1/68
[52] U.S. Cl. .............................. 435/6; 536/26.6
[58] Field of Search ............... 435/6; 536/26.6, 536/24.3, 24.31, 24.32

[56] References Cited

U.S. PATENT DOCUMENTS

| | | | |
|---|---|---|---|
| 5,082,830 | 1/1992 | Brakel et al. | 514/44 |
| 5,800,984 | 9/1998 | Vary | 435/6 |

FOREIGN PATENT DOCUMENTS

| | | | |
|---|---|---|---|
| 97/27317 | 7/1997 | WIPO | C12Q 1/100 |

OTHER PUBLICATIONS

Chalifour, Lorraine E., et al., "A Method for Analysis of Gene expression Patterns," *Analytical Biochemistry* (1994)vol. 216:299–304.

Hong, G.F., "Sequencing of large double–stranded DNA using the dideoxy sequencing technique," *Bioscience Reports* (1982)vol. 2:907–912.

McGraw III, Royal A., "Dideoxy DNA Sequencing with End–Labeled Oligonucleotide Primers," *Analytical Biochemistry* (1984) vol. 143 298–303.

Pietu, Genevieve, et al., "Novel Gene Transcripts Preferentially Expressed in Human Muscles Revealed by Quantitative Hybridization of a High Density cDNA Array," *Genome Research* (1996) vol. 6:492–503.

Raval, Prafulla, "Qualitative and Quantitative Determination of mRNA," *Journal of Pharmacological and Toxicology Methods* (Nov. 1994) vol. 32, No. 3:125–127.

Soares, Marcelo Bento, "Identification and cloning of differentially expressed genes," *Current Opinion in Biotechnology* (1997) vol. 8:542–546.

Stolz, Leslie E., et al., "Hybridization of Biotinylated Oligo(dT) for Eukaryotic mRNA Quantitation," *Molecular Biotechnology* (1996) vol. 6:225–230.

Zhao, Nanding, et al., "High–density cDNA filter analysis: a novel appraoch for large–scale, quantitative analysis of gene expression," *Gene* (1995) vol. 156:207–213.

*Primary Examiner*—Scott W. Houtteman
*Attorney, Agent, or Firm*—Bozicevic, Field & Francis LLP; Bret Field

[57] ABSTRACT

Methods are provided for quantitative gene expression analysis. In the subject methods, end-labeled target nucleic acid is contacted with an array of probe molecules stably associated with the surface of a solid support under hybridization conditions sufficient to produce a hybridization pattern. The resultant hybridization pattern can be used to obtain a quantitative information about the genetic profile of the end-labeled target nucleic acid sample, as well as the physiological source from which it is derived. As such, the subject methods find use in a variety of applications.

17 Claims, 5 Drawing Sheets

A. Schena

B.

A

B

C

QUANTITATIVE MICROARRAY HYBRIDIZATON ASSAYS

INTRODUCTION

1. Technical Field

The field of this invention is gene expression microarrays.

2. Background of the Invention

Microarrays having a plurality of polymeric molecules spatially distributed over, and stably associated with, the surface of a substantially planar substrate, e.g. biochips, are becoming an increasingly important tool in molecular biology, as well as related fields and industries. Microarrays of both polypeptide and polynucleotides have been developed and find use in a variety of applications, such as screening and DNA sequencing. One area in particular in which microarrays find use is in gene expression analysis.

In gene expression analysis with microarrays, an array of "probe" oligonucleotides is contacted with a nucleic acid sample of interest, i.e. target, such as polyA mRNA from a particular tissue type. Contact is carried out under hybridization conditions and unbound nucleic acid is then removed. The resultant pattern of hybridized nucleic acid provides information regarding the genetic profile of the sample tested. Gene expression analysis finds use in a variety of applications, including: the identification of novel expression of genes, the correlation of gene expression to a particular phenotype, screening for disease predisposition, identifying the effect of a particular agent on cellular gene expression, such as in toxicity testing; among other applications.

While current methodologies of gene expression analysis on microarrays are capable of providing a plethora of information regarding the types of genes expressed, they are only capable of yielding such information on a qualitative basis. This is because the labels and labeling schemes used in current methodologies yield a signal which is non-quantitative. As such, to achieve any kind of "quantitative" information regarding gene expression levels, the signal must be compared to a control, which still yields qualitative information and not true quantitative information regarding the copy number of a particular target in a sample.

As such, there continues to be interest in the development of new methodologies of gene expression analysis, where such methodologies that are capable of yielding true quantitative information are of particular interest.

Relevant Literature

Patent References of interest include: U.S. Pat. No. 5,082,830 and WO 97/27317.

Other references of interest include: Schena et al., Science (1995) 467–470; Schena et al., P.N.A.S. U.S.A. (1996) 93: 10614–10616; Pietu et al., Genome Res. (June 1996) 6: 492–503; Zhao et al., Gene (Apr. 24, 1995) 156: 207–213; Soares, Curr. Opin. Biotechnol. (October 1997) 8: 542–546; Raval, J. Pharmacol Toxicol Methods (November 1994) 32: 125–127; Chalifour et al., Anal. Biochem (Feb. 1, 1994) 216: 299–304; Stolz & Tuan, Mol. Biotechnol. (December 19960 6: 225–230; Hong et al., Bioscience Reports (1982) 2: 907; and McGraw, Anal. Biochem. (1984) 143: 298.

SUMMARY OF THE INVENTION

Methods are provided for quantitative gene expression analysis with microarrays. In the subject methods, a hybridization pattern is produced by contacting a probe microarray with a sample of end-labeled target nucleic acid, where each individual end-labeled target nucleic generates the same signal of known value. The hybridization pattern is then detected and used to obtain information, including quantitative information, about the genetic profile of the target nucleic acid sample, as well as the source from which the sample was obtained. The subject methods find use in a variety of applications.

DESCRIPTION OF THE SPECIFIC EMBODIMENTS

Figure 1:
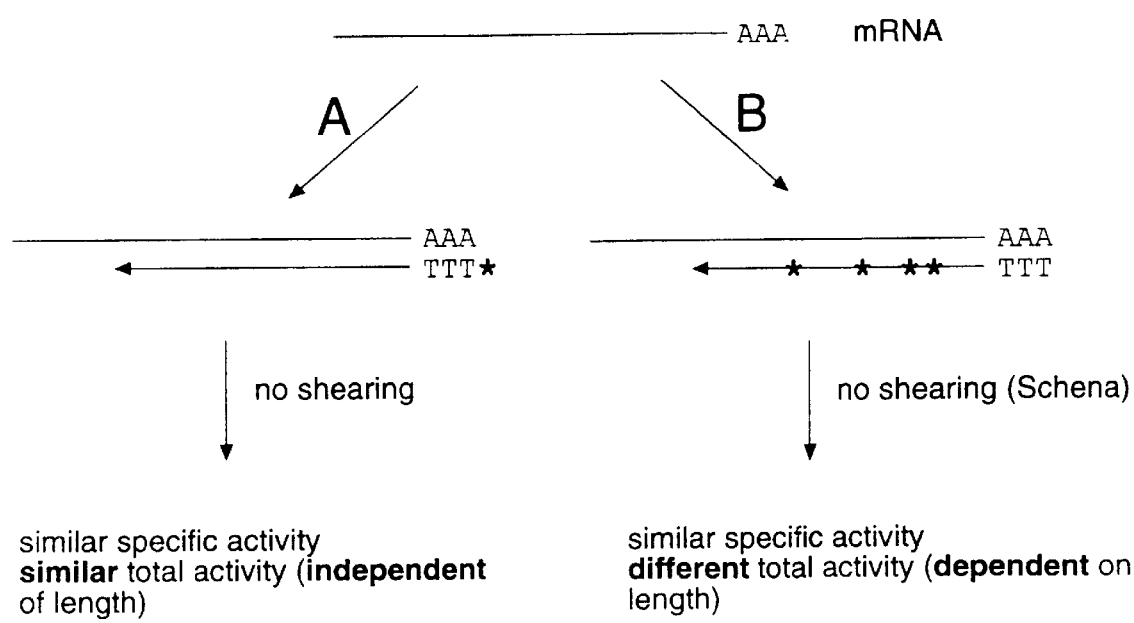
FIG. 1 provides a schematic representation of the labeling approach of the subject invention (labeled A) and the labeling approach of Schena et al., supra, (labeled B).
Figure 2:
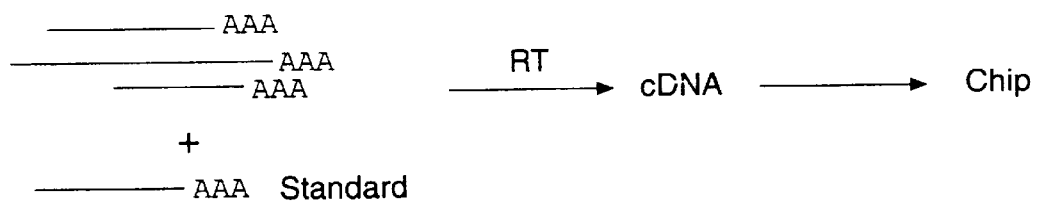
FIG. 2 provides a representation of the prior art standard preparation methodology, see e.g. Schena et al., supra, (marked A) and the standard preparation methodology of the subject invention (marked B).
Figure 2:
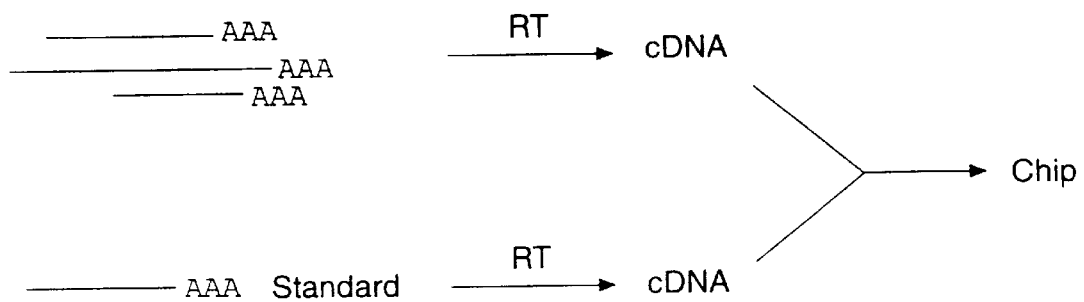
Figure 3:
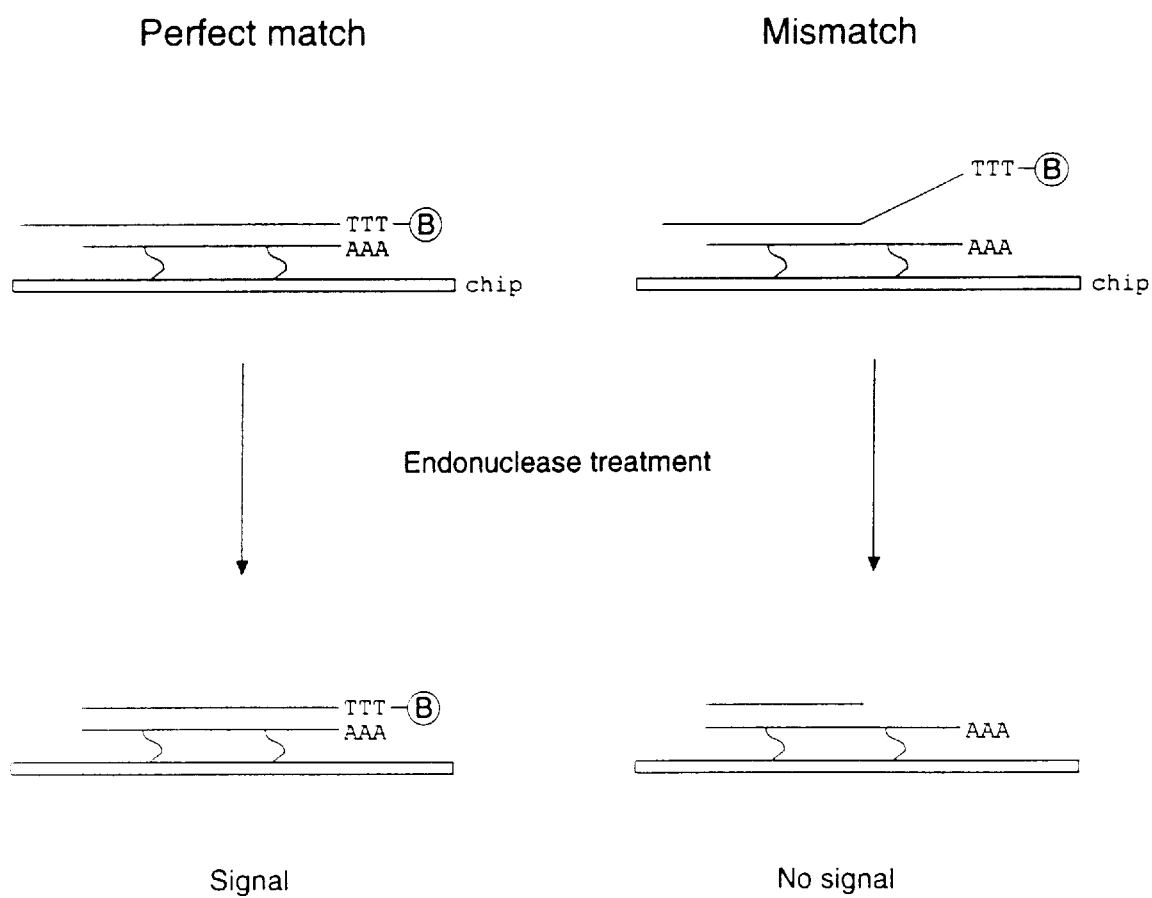
FIG. 3 provides a schematic representation of the nuclease treatment methodology of the subject invention and how it provides for the elimination of mismatched hybridization complexes that yield a false positive signal.
Figure 4:
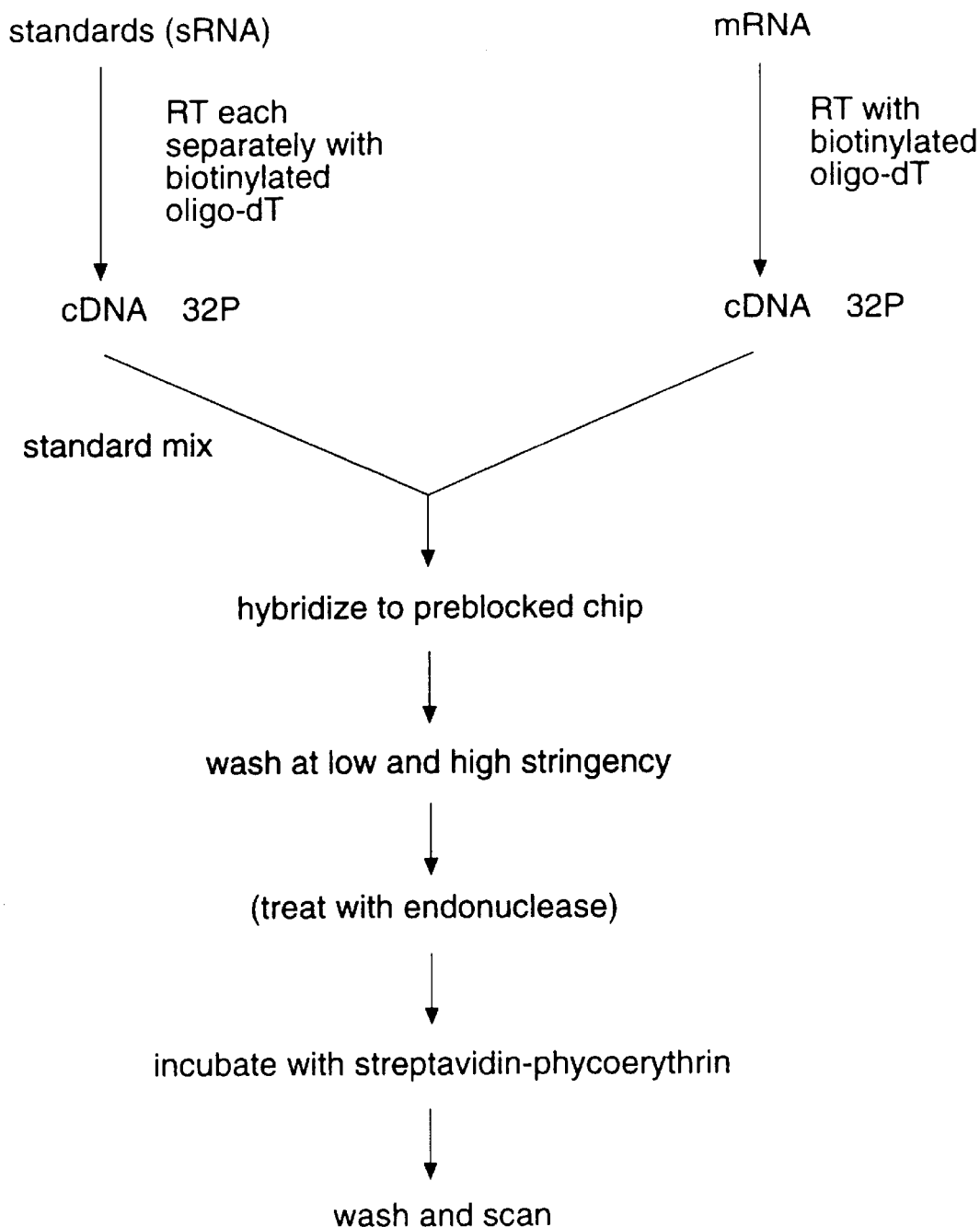
FIG. 4 provides a schematic representation of gene expression analysis according to one embodiment of the subject invention.

Methods of quantitative gene expression analysis are provided. In the subject methods, an array of polynucleotide probes is contacted with a sample of end labeled target nucleic acids to produce a hybridization pattern. The individual target nucleic acids in the sample are all capable of generating the same signal of known value. Thus, each positive signal in the array can be "counted" in order to obtain quantitative information about the genetic profile of the target nucleic acid sample, as well as the physiological source from which it was derived. The subject methods find use in a variety of applications.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

In the subject methods, an array of polynucleotide probes stably associated with the surface of a substantially planar solid support is contacted with a sample of target nucleic acids under hybridization conditions sufficient to produce a hybridization pattern of complementary probe/target complexes. A variety of different arrays which may be used are known in the art. The polymeric or probe molecules of the arrays which are capable of sequence specific hybridization with target nucleic acid may be polynucleotides or hybridizing analogues or mimetics thereof, including: nucleic acids in which the phosphodiester linkage has been replaced with a substitute linkage, such as phophorothioate, methylimino, methylphosphonate, phosphoramidate, guanidine and the like; nucleic acids in which the ribose subunit has been substituted, e.g. hexose phosphodiester; peptide nucleic acids; and the like. The length of the probes will generally range from 10 to 1000 nts, where in some embodiments the probes will be oligonucleotides and usually range from 15 to 150 nts and more usually from 15 to 100 nts in length, and in other embodiments the probes will be longer, usually ranging in length from 150 to 1000 nts, where the polynucleotide probes may be single or double stranded, usually single stranded, and may be PCR fragments amplified from cDNA. The probe molecules on the surface of the substrates will preferably correspond to known genes of the physiological source being analyzed and be positioned on the array at a known location so that positive hybridization events may be correlated to expression of a particular gene in the physiological source from which the target nucleic acid sample is derived. Because of the manner in which the target nucleic acid sample is generated, as described below, the arrays of probes will generally have sequences that are complementary to the non-template strands of the gene to which they correspond. The substrates with which the probe molecules are stably associated may be fabricated from a variety of materials, including plastics, ceramics, metals, gels, membranes, glasses, and the like. The arrays may be produced according to any convenient methodology, such as preforming the probes and then stably associating them with the surface of the support or growing the probes directly on the support. A number of different array configurations and methods for their production are known to those of skill in the art and disclosed in U.S. Pat. Nos: 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; and 5,700,637; the disclosures of which are herein incorporated by reference.

A critical feature of the subject methods is that each of the target nucleic acids in the sample that is contacted with the array during the assay is end-labeled in a manner such that each of the target nucleic acids in the sample a signal of the same specific activity. By generating the same specific activity is meant that each individual target polynucleotide in the sample being assayed is labeled in a manner such that the molecule is capable of providing the same signal, e.g. the same intensity of signal, as every other labeled target in the sample. Each of the target nucleic acids generates a signal of the same specific activity because the number of labeled nucleotide bases in each of the target molecules is either identical or substantially the same, where by substantially the same is meant that the number of labeled nucleotides between any give two target molecules does not vary by more than about 4, usually by not more than about 3 and more usually by no more than about 2. In other words, regardless of the length or specific sequence of a particular target nucleic acid in the sample, it generates a signal of the same specific activity as every other target nucleic acid in the sample.

The term label is used herein to refer to agents that are capable of providing a detectable signal, either directly or through interaction with one or more additional members of a signal producing system. Labels that are directly detectable and may find use in the subject invention include: fluorescent labels, where fluorescers of interest include fluorescers in which the wavelength of light absorbed by the fluorescer will generally range from about 300 to 900 nm, usually from about 400 to 800 nm, where the absorbance maximum will typically occur at a wavelength ranging from about 500 to 800 nm and specific fluorescers of interest for use in singly labeled primers include: fluorescein, rhodamine, BODIPY, cyanine dyes and the like, and are further described in Smith et al, Nature (1986) 321: 647–679; radioactive isotopes, such as $^{32}$S, $^{32}$P, $^{3}$H, etc.; and the like. Examples of labels that provide a detectable signal through interaction with one or more additional members of a signal producing system include capture moieties that specifically bind to complementary binding pair members, where the complementary binding pair members comprise a directly detectable label moiety, such as a fluorescent moiety as described above. Importantly, the label should be such that it does not provide a variable signal, but instead provides a constant and reproducible signal over a given period of time. Capture moieties of interest include ligands, e.g. biotin where the other member of the signal producing system could be fluoresently labeled streptavidin, and the like. Importantly, the target molecules are end-labeled, i.e. the label moiety is present at a region at least proximal to, and preferably at, the 5' terminus of the target.

The end labeled target nucleic acid will generally be a DNA that has been reverse transcribed from RNA derived from a naturally occurring source, where the RNA could be total RNA, polyA+mRNA, amplified RNA and the like, where preferably the RNA is polyA+mRNA. The initial mRNA source may be present in a variety of different samples, where the sample will typically be derived from a physiological source. The physiological source may be derived from a variety of eukaryotic sources, with physiological sources of interest including sources derived from single celled organisms such as yeast and multicellular organisms, including plants and animals, particularly mammals, where the physiological sources from multicellular organisms may be derived from particular organs or tissues of the multicellular organism, or from isolated cells derived therefrom. In obtaining the sample of RNAs to be analyzed from the physiological source from which it is derived, the physiological source may be subjected to a number of different processing steps, where such processing steps might include tissue homogenation, cell isolation and cytoplasmic extraction, nucleic acid extraction and the like, where such processing steps are known to the those of skill in the art. Methods of isolating RNA from cells, tissues, organs or whole organisms are known to those of skill in the art and are described in Maniatis et al., Molecular Cloning: A Laboratory Manual (Cold Spring Harbor Press) (1989).

The mRNA is then reverse transcribed into end-labeled target nucleic acid by hybridizing an appropriately labeled oligo(dT) primer to the mRNA under conditions sufficient for enzymatic extension of the hybridized primer. The primer will be sufficiently long to provide for efficient hybridization to the polyA tail, where the region will typically range in length from 10 to 25 nt in length, usually 10 to 20 nt in length, and more usually from 12 to 18 nt length. Where one wishes to amplify only a portion of the mRNA in the sample, one may optionally provide for a short arbitrary sequence 3' of the oligo dT region, where the short arbitrary sequence will generally be less than 5 nt in length and usually less than 2 nt in length, where the DNTP immediately adjacent to the oligo dT region will not be a dTTP and usually the sequence will comprise no dTTP. Such short 3' arbitrary sequences are described in Ling & Pardee, Science (1992) 257:967. The primer will carry the label, as described above. The label may be attached to one or more of the nucleotides in the primer, either directly or through a linking group, as is known in the art. In a preferred embodiment in which the label is biotin, the number of biotinylated dNTPs in the primer will be at least 1 and may be as high as 12, but will usually be about 7. In preparing the end-labeled target nucleic acid, the primer is contacted with the mRNA with a reverse transcriptase and other reagents necessary for primer extension under conditions sufficient for first strand cDNA synthesis, where additional reagents include: dNTPs; buffering agents, e.g. Tris.Cl; cationic sources, both monovalent and divalent, e.g. KCl, $MgCl_2$; RNAase inhibitor and sulfhydryl reagents, e.g. dithiothreitol; and the like. A variety of enzymes, usually DNA polymerases, possessing reverse transcriptase activity can be used for the first strand cDNA synthesis step. Examples of suitable DNA polymerases include the DNA polymerases derived from organisms selected from the group consisting of a thermophilic bacteria and archaebacteria, retroviruses, yeasts, Neurosporas, Drosophilas, primates and rodents. Preferably, the DNA polymerase will be selected from the group consisting of Moloney murine leukemia virus (M-MLV) as described in U.S. Pat. No. 4,943,531 and M-MLV reverse transcriptase lacking RNaseH activity as described in U.S. Pat. No. 5,405,776 (the disclosures of which patents are herein incorporated by reference), human T-cell leukemia virus type I ( HTLV-I), bovine leukemia virus (BLV), *Rous sarcoma* virus (RSV), human immunodeficiency virus (HIV) and *Thermus aquaticus* (Taq) or *Thermus thermophilus* (Tth) as described in U.S. Pat. No. 5,322,770, the disclosure of which is herein incorporated by reference, avian reverse transcriptase, and the like. Suitable DNA polymerases possessing reverse transcriptase activity may be isolated from an organism, obtained commercially or obtained from cells which express high levels of cloned genes encoding the polymerases by methods known to those of skill in the art, where the particular manner of obtaining the polymerase will be chosen based primarily on factors such as convenience, cost, availability and the like. Of particular interest because of their commercial availability and well characterized properties are avian reverse transcriptase and M-MLV. The order in which the reagents are combined may be modified as desired. One protocol that may used involves the combination of all reagents except for the reverse transcriptase on ice, then adding the reverse transcriptase and mixing at around 4° C. Following mixing, the temperature of the reaction mixture is raised to 37° C. followed by incubation for a period of time sufficient for first strand cDNA primer extension product to form, usually about 1 hour.

In performing the assays of the subject invention, the end-labeled target nucleic acid is contacted with the array under conditions sufficient for hybridization of target nucleic acid to probe to occur. Suitable hybridization conditions are well known to those of skill in the art and reviewed in Maniatis et al, supra and WO 95/21944, where the conditions can be modulated to achieve a desired specificity in hybridization, e.g. highly stringent or moderately stringent conditions. For example, low stringency hybridization conditions may be at 50° C. and 6×SSC (0.9 M sodium chloride/0.09 M sodium citrate) while hybridization under stringent conditions may be at 50° C. or higher and 0.1×SSC (15 mM sodium chloride/01.5 mM sodium citrate).

In some applications, it is desired to analyze populations of labeled nucleic acids from two or more physiological sources. In analyzing the differences in the population of labeled nucleic acids generated from two or more physiological sources according to the subject invention, a population of end labeled targets nucleic acids from each physiological source of interest is generated as described above and each population of labeled nucleic acids are separately contacted to identical probe arrays under conditions of hybridization, preferably under stringent hybridization conditions, such that labeled nucleic acids hybridize to their complementary probes on the substrate surface.

Where all of the target sequences comprise the same label, different arrays will be employed for each physiological source (where different could include using the same array at different times). Alternatively, where the labels of the targets are different and distinguishable for each of the different physiological sources being assayed, the opportunity arises to use the same array at the same time for each of the different target populations.

In many instances, it is desirable to include in the sample of target nucleic acids that is contacted with the array a labeled set of standard DNA molecules that are present in known amounts and can be used as calibrating agents in subsequent analysis. One means of providing for the presence of this labeled DNA standard in the sample of target nucleic acids is to "spike" the RNA sample prior to reverse transcription into end-labeled target with a set of RNA molecules of defined ratios, i.e. standard RNA.

Alternatively and preferably, the standard will be provided by reverse transcribing the standard RNA into end-labeled DNA separately from the sample mRNA under conditions substantially the same as, and preferably identical to, the conditions used to prepare the labeled target nucleic acid sample. The resultant end-labeled standard is then combined with the target to produce a standard comprising end-labeled target nucleic acid sample for subsequent contact with the array.

Following hybridization, where non-hybridized labeled nucleic acid is capable of emitting a signal during the detection step, a washing step is employed where unhybridized labeled nucleic acid is removed from the support surface, generating a pattern of hybridized nucleic acid on the substrate surface. A variety of wash solutions and protocols for their use are known to those of skill in the art and may be used.

Where the label on the target nucleic acid is not directly detectable, one then contacts the array, now comprising bound target, with the other member(s) of the signal producing system that is being employed. For example, where the label on the target is biotin, one then contacts the array with streptavidin-fluorescer conjugate under conditions sufficient for binding between the specific binding member pairs to occur. Following contact, any unbound members of the signal producing system will then be removed, e.g. by washing. The specific wash conditions employed will necessarily depend on the specific nature of the signal producing system that is employed, and will be known to those of skill in the art familiar with the particular signal producing system employed.

The resultant hybridization pattern(s) of labeled nucleic acids may be visualized or detected in a variety of ways, with the particular manner of detection being chosen based on the particular label of the nucleic acid, where representative detection means include scintillation counting, autoradiography, fluorescence measurement, calorimetric measurement, light emission measurement and the like.

Prior to detection or visualization, where one desires to reduce the potential for a mismatch hybridization event to generate a false positive signal on the pattern, the array of hybridized target/probe complexes may be treated with an endonuclease under conditions sufficient such that the endonuclease degrades single stranded, but not double stranded DNA. A variety of different endonucleases are known and may be used, where such nucleases include: mung bean nuclease, S1 nuclease, and the like. Where such treatment is employed in an assay in which the target nucleic acids are not labeled with a directly detectable label, e.g. in an assay with biotinylated target nucleic acids, the endonuclease treatment will generally be performed prior to contact of the array with the other member(s) of the signal producing system, e.g. fluorescent-streptavidin conjugate. Endonuclease treatment, as described above, ensures that only end-labeled target/probe complexes having a substantially complete hybridization at the 3' end of the probe are detected in the hybridization pattern.

Following hybridization and any washing step(s) and/or subsequent treatments, as described above, the resultant hybridization pattern is detected. In detecting or visualizing the hybridization pattern, the intensity or signal value of the label will be not only be detected but quantified, by which is meant that the signal from each spot of the hybridization will be measured and compared to a unit value corresponding the signal emitted by known number of end labeled target nucleic acids to obtain a count or absolute value of the copy number of each end-labeled target that is hybridized to a particular spot on the array in the hybridization pattern.

Following detection or visualization, the hybridization pattern can be used to determine quantitative information about the genetic profile of the labeled target nucleic acid sample that was contacted with the array to generate the hybridization pattern, as well as the physiological source from which the labeled target nucleic acid sample was derived. By genetic profile is meant information regarding the types of nucleic acids present in the sample, e.g. in terms of the types of genes to which they are complementary, as well as the copy number of each particular nucleic acid in the sample. From this data, one can also derive information about the physiological source from which the target nucleic acid sample was derived, such as the types of genes expressed in the tissue or cell which is the physiological source, as well as the levels of expression of each gene, particularly in quantitative terms. Where one uses the subject methods in comparing target nucleic acids from two or more physiological sources, the hybridization patterns may be compared to identify differences between the patterns. Where arrays in which each of the different probes corresponds to a known gene are employed, any discrepancies can be related to a differential expression of a particular gene in the physiological sources being compared. Thus, the subject methods find use in differential gene expression assays, where one may use the subject methods in the differential expression analysis of: (a) diseased and normal tissue, e.g. neoplastic and normal tissue, (b) different tissue or subtissue types; and the like.

Also provided are kits for carrying out the subject invention, where such kits at least include end-labeled primer as described above and instructional material for carrying out the subject methodology, where the instructional material could be present on a package insert, on one or more containers in kit and/or packaging associated with the kit. The kits may also include one or more additional components necessary for carrying at the gene expression assay of the subject invention, where such additional components include: enzymes, e.g. polymerases, reverse transcriptases, endonucleases, dNTPs, buffer medium, and the like. The kits may further comprise one or more probe arrays.

The following examples are offered by way of illustration and not by way of limitation.

Experimental

Five cloned *Arabidopsis thaliana* genes ranging from 0.5 to 1 kb were selected as standards. These genes were PCR amplified from plasmid DNA using a 5' primer containing a T7 promoter sequence and a 3' primer containing a poly dT sequence under standard conditions. The primer sequences were:

```
5'
Arab2-T7      CGGTCGACTAATACGACTCACTATAGGGAGAAAGTTCAACAGAAGATG

Arab4-T7      CGGAATTCTAATACGACTCACTATAGGGTCTTGATGATTCATGCA

Arab6-T7      CGGAATTCTAATACGACTCACTATAGGGATCGATTACTCCACATACC

Arab8-T7      CGGAATTCTAATACGACTCACTATAGGGATCTGAAGTCCTCGGAAG

Arab9-T7      CGGAATTCTAATACGACTCACTATAGGGTAGTAGACGAAGGTTATAAC

3'
Arab2-polyA   T20AACTACATGCATATCTGGTCC

Arab4-polyA   T20TACCGTAATACATATTCGAAG

Arab6-polyA   T20GATTTCAAGTTCTTATGG

Arab8-polyA   T20AACTGATAAAACTTGGCTC

Arab9-polyA   T20AGTCCTTAAAAAGCATGGAAG
```

The PCR products were gel purified using Geneclean (BIO101) and T7 in vitro transcription reactions were performed using the Ampliscribe transcription kit (Epicentre Technologies). The resulting sense RNAs were LiCl precipitated, resuspended in water, and re-precipitated with ammonium acetate/ethanol. A first strand cDNA reaction was performed separately for each sRNA using the Superscript Choice cDNA synthesis system (Gibco BRL), $^{32}$P-dCTP, and biotinylated dT primers (3B or 7B).

```
3B  BAGACTCGABGCTAGCGABCTCGT18V

7B
BAGTGGTCTBATCAGCAGBGCTATCCTBCTCACTGGBTCGTAATCBCAAGCAC

ABGCAGT18V ("B'9 = biotin)
``` cDNA yields were determined by TCA precipitation. Each cDNA was heated at 70° C. for 15 min after addition of 1 µl 0.5 M EDTA and 5 µl 1 N NaOH. Each reaction was then further processed by addition of 5 µl 1 M Tris, pH 7.4 and 5 µl 1 M HCl, phenol/CHCl₃ extraction, and ammonium acetate/ethanol precipitation. The cDNAs were resuspended in water, re-quantitated by TCA precipitation, and diluted in 100 µg/ml salmon sperm DNA to 20× stock concentrations. All 5 standard cDNA 20× stocks were used to make a ST-HYB solution (5× SSC, 100 µg/ml denatured salmon sperm DNA, 3% PEG$_{8000}$, 0.4% SDS, 100 µg/ml yeast tRNA, 1 mg/ml BSA). The final concentration of each Arabidopsis standard was different in the ST-HYB solution and ranged between 5 and 400 pM.

II. Complex Sample Precipitation

1 µg of poly A$^+$RNA from THP-I cells (ATCC TIB 202) was reverse-transcribed using either the 3B or 7B primers, quantitated by TCA precipitation, and processed in the same manner as the Arabidopsis standards. After the final precipitation, the complex sample was resuspended in 3–5 µl of the ST-HYB buffer (see above).

III. Microarray Fabrication

Microarrays were fabricated using a Biodot spotting apparatus and aldehyde-coated glass slides (CEL Associates). PCR products were amplified, spotted onto the aldehyde-coated slides, and processed according to published procedures (Schena, et al., PNAS USA (1996) 93: 10614–10619). The PCR products included the series of Arabidopsis standards along with other human genes.

IV. Hybridization and Analysis

Figure 5:
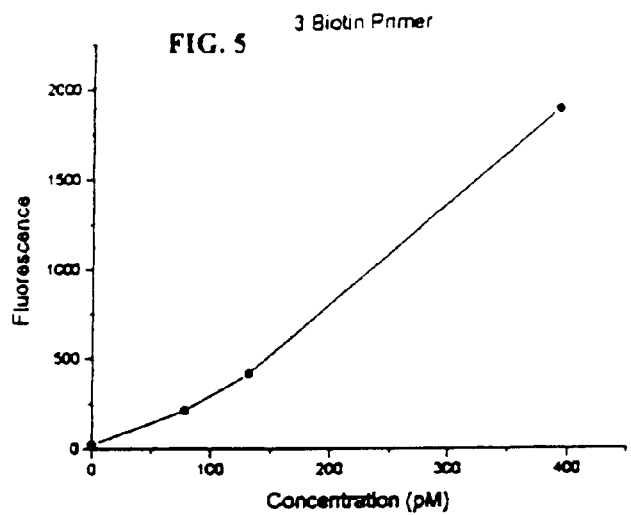
FIGS. 5A to 5C provides standard curves resulting from the use of a 3b primer, a 7b primer and both in combination, in accordance with the subject invention.
Figure 5:
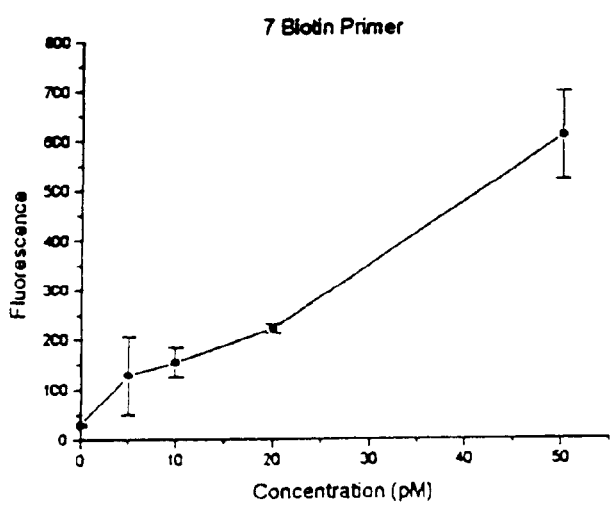
Figure 5:
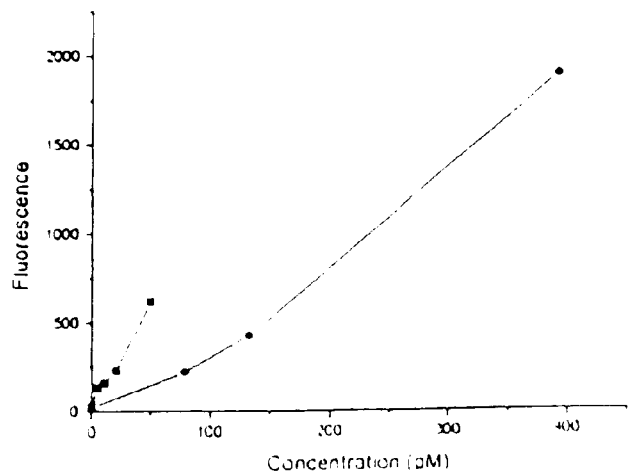

Microarrays were prehybridized in buffer (5× SSC, 100 µg/ml denatured salmon sperm DNA, 1% SDS, 100 µg/ml yeast tRNA, 1 mg/ml BSA) for at least 1 hour at 60° C. in a humified chamber. The slides were then rinsed once in 1× SSC/0.2% SDS, once in water, and dried with compressed air. The slides were then hybridized with 3–5 µl ST-HYB (with or without complex sample) at 60° C. for 12–14 hours. After hybridization, the slides were washed once with 1× SSC/0.2% SDS 5 min at room temperature (RT), once with 0.1× SSC/0.2% SDS 15 min at RT, once with 0.1× SSC/0.2% SDS 15 min at 40–50° C., rinsed once in 0.1× SSC and dried with compressed air. The slides were rinsed with 1× SSC/0.002% Triton X-100, blocked with 1 mg/ml BSA in 1× SSC/0.002% Triton X-100 15 min at RT, and incubated with stain solution (20 µg/ml. streptavidin-coupled R-phycoerythrin (Molecular Probes), 1 mg/ml BSA, 1× SSC/0.002% Triton X-100) 15 min at RT. The slides were then washed in 1× SSC/0.002% Triton X-100 15 min at RT and scanned wet in the same buffer using the Fluroscan H scanner (Incyte Pharmaceuticals). Image analysis was performed using the Dualscan software (Incyte Pharmaceuticals). FIG. 5. TOP panel. Standard curve using the 3B primer (one microarray). Middle panel. Standard curve using the 7B primer (average of two microarrays). Bottom panel. Combination of the standard curves from the top and middle panels. Each point on the standard curves represents a different Arabidopsis gene.

V. Nuclease Digestion

After the final hybridization wash but prior to the staining procedure, microarray slides are washed with 1× mung bean nuclease buffer (New England Biolabs) at RT for 5 min. Five μl of 1× mung bean nuclease buffer containing 1 unit of mung bean miclease was added to each microarray and allowed to incubate for 30 min at RT. Microarrays were then rinsed thoroughly with 1×SSC/0.002% Triton X-100 at RT for 5 min and stained as described above.

It is evident from the above discussion and results that a number of advantages are provided by the subject invention. First, the subject invention provides for obtaining quantitative, and not just qualitative, information about a sample of target nucleic acids, as well as about the physiological source from which it was derived. Second, preparation of standards according to the preferred embodiment of the subject invention yields reproducible results and avoids problems of stability. Third, treatment of the hybridized target with endonuclease prior to pattern detection provides for discrimination between two or more highly related target species, thereby reducing problems associated with mismatch hybridization.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A hybridization assay comprising the steps of:
    contacting an array of probe molecules stably associated with the surface of a solid support with an end labeled target nucleic acid sample under hybridization conditions sufficient to produce a hybridization pattern, wherein each of said end labeled target nucleic acids is capable of generating a signal of substantially the same specific activity; and
    detecting said hybridization pattern.

2. The assay according to claim 1 further comprising the steps of removing unhybridized target nucleic acid prior to said detecting step.

3. The assay according to claim 1, wherein said method further comprises preparing said end labeled target nucleic acid sample by contacting an mRNA source with an end-labeled oligo(dT) primer, a reverse transcriptase and nucleotides under conditions sufficient for reverse transcription of said mRNA into said end-labeled target nucleic acid sample, wherein said-labeled oligo(dT) primer comprises a known number of labeled nucloetides.

4. The assay according to claim 1, wherein said end-labeled nucleic acid sample further comprises end-labeled standard DNA.

5. The assay according to claim 4, wherein said assay further comprises:
    (a) preparing said end-labeled standard DNA by contacting a standard RNA sample with said end-labeled oligo(dT) primer, a reverse transcriptase and nucleotides under conditions sufficient for reverse transcription of said standard RNA into said end labeled standard DNA; and
    (b) combining said end labeled standard DNA with said end-labeled target nucleic acid sample.

6. The assay according to claim 1, wherein said array is contacted with a nuclease prior to said detecting step.

7. An assay to determine the genetic profile of a physiological source, said assay comprising the steps of:
    (a) preparing an end labeled target nucleic acid sample by contacting mRNA from a physiological source with an end-labeled oligo(dT) primer, a reverse transcriptase and nucleotides under conditions sufficient for reverse transcription of said mRNA into said end-labeled target nucleic acid sample, wherein said end-labeled oligo (dT) primer is comprises a known number of labeled nucleotides;
    (b) preparing end labeled standard DNA by contacting standard RNA with said end-labeled oligo(dT) primer, a reverse transcriptase and nucleotides under conditions sufficient for reverse transcription of said standard RNA into said end labeled standard DNA;
    (c) combining said end labeled standard DNA with said end-labeled target nucleic acid sample;
    (d) contacting said end labeled target nucleic acid sample with an array of probe molecules stably associated with the surface of a solid support under hybridization conditions to produce a hybridization pattern;
    (e) separating unhybridized target from said array;
    (f) contacting said array with a nuclease; and
    (g) detecting said hybridization pattern.

8. The assay according to claim 7, wherein said end-labeled target nucleic acids are not directly detectable and said method further comprises contacting said hybridization pattern with at least one additional member of a signal producing system to provide a detectable hybridization pattern.

9. The assay according to claim 8, wherein said contacting with at least one additional member of a signal producing system is prior to said step (f).

10. The assay according to claim 8, wherein said end-labeled target nucleic acids are labeled with biotin.

11. The assay according to claim 9, wherein said at least one additional member of a signal producing system is fluorescently labeled streptavidin.

12. A kit for use in the preparation of end-labeled target nucleic acids to be used in an array based assay, said kit comprising:
    end labeled oligo(dT) primers capable of generating a signal of known value; and a polymerase.

13. The kit according to claim 12, wherein said kit further comprises nucleotides.

14. The kit according to claim 12, wherein said kit further comprises a buffer.

15. The kit according to claim 12, wherein said kit further comprises an array of probe molecules and said kit is for use in a hybridization assay.

16. The kit according to claim 12, wherein said kit further comprises standard RNA.

17. The kit according to claim 12, wherein said kit further comprises a nuclease.

* * * * *